(12) United States Patent
Petrus

(10) Patent No.: US 6,930,099 B2
(45) Date of Patent: *Aug. 16, 2005

(54) COMPOSITION FOR THE TREATMENT AND PREVENTION OF ENDOTHELIAL DYSFUNCTION

(75) Inventor: Edward J. Petrus, Austin, TX (US)

(73) Assignee: Advanced Medical Instruments, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/436,528

(22) Filed: May 14, 2003

(65) Prior Publication Data

US 2003/0215430 A1 Nov. 20, 2003

Related U.S. Application Data

(63) Continuation-in-part of application No. 09/947,674, filed on Sep. 7, 2001, now Pat. No. 6,596,708.

(51) Int. Cl.⁷ .................... A61K 31/7008; A61K 31/70; A61K 31/60; A61K 31/375
(52) U.S. Cl. .................... 514/62; 514/168; 514/165; 514/474; 514/494; 424/641; 424/643; 536/55.2
(58) Field of Search .................... 514/62, 168, 165, 514/494, 725, 474; 424/464, 682, 702, 641, 643; 536/55.2

(56) References Cited

U.S. PATENT DOCUMENTS 6,013,280 A * 1/2000 Frisbee et al. .............. 424/464

OTHER PUBLICATIONS

Drugstore.com (http://www.drugstore.com/qxp78764_333181_sespider/knox/nutra_joint_gelatine_plus_glucosamine_unflavored.htm; pp. 1–3, copyright 1999).*

Chambers JC, Improved Vascular Endothelial Function After Oral B Vitamins. Circulation 2000;102:2479–2483.

Whelton PK, Potassium In Preventing And Treating High Blood Pressure Semin Nephrol Sep. 1999:19(5)494–9.

Vita JA, Ascorbic Acid Improves Vasodilation In Patients with CAD. Circulation 1999;99:3234–3240.

Vasdev S, Dietary Alpha–Lipoic Acid Supplementation Lowers BP In spontaneously Hypertansive Rats, J Hypertens May 18, 2000(5)567–73.

Taddei S, Endothelial Dysfunction In Hypertension; Fact Or Fancy? J. Cardiovasc Pharmacol 1998;32 Suppl. 3 S41–7.

Siani A, Blood Pressure And Metabolic Changes During Dietary L–Arginine Supplementation In Humans, Am J Hypertens May 13, 2000(5 Pt 1)547–51.

Miller, ER, Meta–Analysis Supports / Inverse Link Between Magnesium Intake and BP. Am J Hypertens 2002; 15:691–696.

Fotherby MD, Long–Term Potassium Supplementation Lowers B P In Elderly Hypertensive Subjects Int J Clin Pract Jun. 1997 51(4)219–22.

Figulla HR, Vitamin C Reverses Impaired Endothelial Function in Cardiomyopathy Am J Cardiol 2001;88:1001–1005.

Guerci B, Endothelial Dysfunction And Type 2 Diabetes, Diabetes Metab (Paris) 2001, 27, 436–447.

* cited by examiner

Primary Examiner—James O. Wilson
Assistant Examiner—Michael C. Henry

(57) ABSTRACT

This invention relates to a method and compositions for the treatment and prevention of disorders associated with endothelial dysfunction consisting of anti-inflammatory agents and dietary supplements.

18 Claims, No Drawings

COMPOSITION FOR THE TREATMENT AND PREVENTION OF ENDOTHELIAL DYSFUNCTION

This application is a continuation-in-part of Ser. No. 09/947,674 filed Sep. 7, 2001 now U.S. Pat. No. 6,596,708.

FIELD OF INVENTION

This invention involves compositions of therapeutic agents for the treatment and prevention of disorders associated with endothelial dysfunction.

BACKGROUND OF THE INVENTION

Endothelial cells are mesodermally derived, simple squamous epithelial cells that line the heart, blood and lymph vessels, line any closed cavity (peritoneal, pleural, pericardial, synovial) and line the intestinal tract. Endothelial cells of blood vessels have both mechanical and functional properties. They provide a barrier effect to the penetration of blood components into the vessel wall and have endocrine functions.

Vascular endothelium is a multi-functional barrier separating blood from interstitium. It plays a role in coagulation, inflammation, angiogenesis and has vasomotor functions. Endothelial dysfunction can be considered as an initial stage of atherosclerosis. Malik J, Melenovsky V, Wichterle D, Function and dysfunction of the endothelium, *Cas Lek Cesk* 2000 Apr. 12;139(7):197–202. Endothelium dysfunction is recognized as an early event in the pathogenesis of cardiovascular disease, and linked to hypertension, diabetes mellitus and oxidative stress. Pepine C J, Clinical implications of endothelial dysfunction, *Clin Cardiol* 1998 November;21(11):795–9.

Endothelial dysfunction is characterized by a loss of barrier function and an infiltration of cellular material into the vascular wall and loss of physiological vascular tone. There is a loss of nitric oxide mediated physiological vasodilation, increased endothelial adhesion and migration of leucocytes and macrophages into the subendothelial vascular wall. Hypoxia, shear forces and oxidative stress trigger events for endothelial dysfunction. Disorders associated with endothelial dysfunction include; hypertension, atherosclerosis, diabetes, immune system dysfunction, infections, inflammations, cardiovascular disease and stroke.

SUMMARY OF THE INVENTION

This invention relates to a method and compositions for the treatment and prevention of disorders associated with endothelial dysfunction consisting of anti-inflammatory agents and dietary supplements.

DETAILED DESCRIPTION OF THE INVENTION

Each year 1.5 million Americans suffer heart attacks (myocardial infarction) and 500,000 die of that first attack, with 48% being females. Most of the 500,000 deaths occur within 2 hours after chest pain or other symptoms. In Britain half of all heart attack patients die within two hours of symptom onset and two-thirds of the deaths occur before admission to the hospital. Rawles J, *Pre-Hospital Immediate Care* 1997;1:12–18. During this critical 120 minute period, coronary thrombosis could be eliminated and the heart attack prevented if the thrombus could be averted. While the nation's death rate from heart attacks peaked in the 1960s, when the death rate from heart disease was 307.4 per 100,000 people, the rate has plummeted to 134.6 in 1996, but myocardial infarction still ranks as the nation's leading killer. Coronary artery disease (CAD) affects 13.5 million Americans, a million have survived heart attacks, 7 million have angina (myocardial ischemia), 600,000 have undergone coronary bypass surgery and 2,000 have had heart transplants. The economic burden is estimated at $150 billion annually. Tindall W N, *Business & Health* February 1998.

The vascular endothelium modulates blood vessel tone by secreting a variety of dilating and constricting substances. Dilating agents include nitric oxide (NO), prostacyclin, bradykinin, and endothelium-derived relaxing factor (EDRF) and heparinoids; constricting agents include endothelin, superoxide anion, endothelium-derived constricting factor, locally produced antiotensin II, and thromboxane. These agents not only control and alter vascular tone, but also can affect platelet adhesion and aggregation, influence thrombogenicity of the blood, and participate in cell proliferation and the development and progression of atherosclerosis.

Injury to endothelial cell function, primarily resulting from increased oxidant stress within the endothelium, leads to a cascade of events beginning with activation of vascular cytokines such as interleukin-1 (IL-1) and tumor necrosis factor-$\alpha$ (TNF-$\alpha$) and proceeding to expression of adhesion molecules on the cell surface that include vascular cell adhesion molecule-1 (VCAM-1), intercellular adhesion molecule-1 (ICAM-1), and endothelial-leucocyte adhesion molecule (ELAM), which attracts monocytes and other leucocytes to adhere to the endothelial surface. Adherence is followed by infiltration of mononuclear cells into the vascular wall, together with activation of monocyte chemoattractant protein-1 (MCP-1), leads to scavenging of oxidized low-density lipoproteins (LDL), formation of lipid-laden foam cells, and development or progression of atherosclerotic plaque. Activation of prothrombogenic stimuli and inactivation of fibrinolytic factors with endothelial dysfunction predisposes these blood vessels to thrombosis. Quyyumi A A, *Am J of Med* 1998;105(1A):32S–39S.

Vascular injury triggers thrombosis and a proliferative response. By the release of tissue factor and exposure of subendothelial matrix, the coagulation and platelet pathways are activated and a thrombus is formed, either on a micro or macroendoluminal level. Additionally, platelet activation leads to a variety of mitogens, growth-promoting factors, and cytokines. Potent mitogens, such as platelet-derived growth factor and fibroblast growth factor, cause smooth muscle cells, fibroblasts, inflammatory cells, and endothelial cells to participate in re-endothelization. Smooth muscle cell and fibroblast proliferation and migration result from signal transduction pathways initiated by factors biding to their specific cell-surface receptor. Smooth muscle cells and fibroblasts migrate from the media to the intimal surface. Smooth muscle cells are phenotypically transformed to the synthetic subtype and secrete an extracellular matrix consisting of proteoglycans. Ward S R, Topol E J, *Resident & Staff Physician* 1995;41(3):11–18.

British scientists have reported a well-established link between inflammation and cardiovascular events mediated by inflammation-induced dysfunction of the arterial endothelium. Even mild systemic inflammatory responses are associated with significant alteration in endothelial function which lead to increased cardiovascular risk. Hingorani A D, et al., *Circulation* 2000;102:994–999.

Thrombus formation is the proximate cause of myocardial infarction, but atherosclerosis, the chief underlying cause, is a chronic disease that progresses over decades of life. Inflammation has a role in both the initiation and the progression of atherosclerosis, and anti-inflammatory agents have a role in the prevention of cardiovascular disease.

Atherosclerosis may be considered as an aberrant form of would-healing in arteries. Repeated minor trauma, leading to subendothelial hemorrhage, may well account for the tendency of atherosclerosis to occur mostly at major blood vessel flexion sites and at sites of mechanical stress, such as the carotid sinus or the bifurcation of the carotid artery. The positive injury potential resulting from petechial hemorrhages in the vascular intima will attract negatively charged platelets an leucocytes and will lead to a layered thrombus formation. Gaps between the endothelial cells of the intima will allow the insinuation of monocytes beneath the endothelium, where it seems they can become transformed into macrophages and engulf oxidized LDL to become foam cells and lead to the formation of the atherosclerotic plaque.

C-reactive protein (CRP) is a natural substance that results from an inflammatory response to injury of infection by mobilizing white blood cells. CRP is an acute-phase reactant that is a marker for underlying systemic inflammation, reported in patients with acute ischemia or myocardial ischemia and found to predict recurrent ischemia in those with unstable angina. Base-line levels of CRP in apparently healthy men can predict the risk of the first myocardial infarction and ischemic stroke. Previous infection with *Chlamydia pneumonia, Heliobacter pylori*, herpes simplex virus, or cytomegalovirus may be the source of the chronic inflammation detected by CRP. The rates of myocardial infarction were lower for those on acetylsalicylic acid (ASA) for all levels of CRP. Ridker P M, et al, *NEJM* 336(14):973–979. An elevated CRP level is related to inflammation, and increased inflammation is noted for many diseases, such as cancer, cardiovascular disease, infection, connective tissue diseases and injuries. Elevated CRP reflects an increased production of proinflammatory cytokines such as interleukin-6, which may be contributing to the pathophysiology of disease either directly or indirectly through their relationship to other important components of inflammation, thrombosis, or fibrinolysis. Kuller L H, Tracy R P, *Arteriosclerosis, Thrombosis, and Vascular Biology* 2000;20(4):901

The Physicians Health Study (PHS) indicates that healthy men with baseline levels of CRP in the highest quartile had a threefold increase in risk of developing future myocardial infarction and twice the risk of developing stroke. These risk estimates were stable over an 8–10 year follow-up period, were not modified by smoking status, and were independent of other cardiovascular risk factors, including total and HDL cholesterol, triglycerides, lipoproteins and fibrinogen. Elevated baseline levels of CRP are also associated with a fourfold increase in the risk of developing clinically severe peripheral arterial disease, again independent of usual risk factors. Plasma levels of ICAM-1 are elevated many years in advance of a first-ever myocardial infarction and that levels of ICAM-1 correlate with CRP. Cellular adhesion molecules, such as ICAM-1, are critical in the adhesion of circulating leucocytes to the endothelial cell and subsequent endothelial transmigration, and provide evidence that cellular mediators of inflammation have a critical role in atherogenesis. CRP levels increase with increasing prevalence of exposure to *Heliobactor pylori*, the bacteria responsible for gastric ulcers. Ridker P M, *Circulation* 1998;97: 1671–1674.

Chronic subclinical infection with *Chlamydia pneumoniae, Helicbacter pylori*, chronic bronchitis, and chronic dental sepsis have been associated with raised values of CRP and have been implicated as risk factors for coronary heart disease. Mendall M A, *BMJ* 1998;316:953–954. During acute unstable angina, which if believed to be an immune system-mediated inflammatory disorder, patients had significantly greater levels of CRP and helper T-cells and significantly reduced levels of suppressor T-cells. Caligiuri G, *J Am Coll Cardiol* 1998;32:1295–1304.

*H pylori* is a spiral gram-negative rod that resides beneath the gastric mucus layer adjacent to epithelial cells. It causes a chronic mucosal inflammation and associated with peptic ulcer disease. *H pylori* is treated with antibiotics and bismuth or bismuth containing compounds such as bismuth subsalicylate. Tierney Jr. L M, McPhee S J, Papadakis M A, Current Medical Diagnosis and Treatment, Appelton & Lange, 3$^{rd}$ ed 1994 p.490.

CRP concentrations were increased in about 75% of patients within 24 hours after ischemic stroke, and higher values were significantly associated with large infarct size. Di Napoli M, *BMJ* 2001;322:1605. In 1950, the stroke death rate per 100,000 was 88.8. In 1996, it was 26.5. Stroke is the third leading cause of death (after heart disease and cancer). Americans suffer about 500,000 strokes each year and 150,000 stroke deaths. Cerebral thrombosis and cerebral embolism, known as ischemic stroke, account for about 80% of strokes. Cerebral thrombosis often occurs at night or first thing in the morning when blood pressure is normally low. About one-third of those who experience a transient ischemic attack (TIA) have a stroke within five years. Half of the post-TIA strokes occur within a year, 20% within one month. TIAs double the risk of heart attack. Those on ASA had 42% fewer strokes. It has been reported that immediate use of ASA be considered in all patients with acute ischemic stroke. Sandercock P A G, *Lancet* 1997;349:1563–1565, 1569–1581.

Many of the current studies point to an inflammatory etiology for cardiovascular and cerebrovascular disorders. Anti-inflammatory agents have shown benefits for the treatment and prevention of these endothelial dysfunction diseases. This invention provides a composition to overcome the obstacles inherent in the prior approaches.

Acetylsalicylic acid (ASA) has been known to treat and prevent cardiovascular disease by reducing thrombosis, but the real effect is as an anti-inflammatory agent. ASA inhibits cyclo-oxygenase in both platelets and endothelial cells. At low doses ASA inhibits the formation of thromboxane A2 (TXA2), a potent vasoconstrictor and platelet agonist formed via cyclo-oxygenase-dependent pathway in platelets. At higher doses, ASA has been shown to block the formation of prostacyclin (PGI2), a vasodilator and inhibitor of platelet aggregation, in endothelial cells.

The use of ASA for the primary prevention of CAD was examined in the PHS in which 22,000 US male physicians were observed for about 5 years. Those who took 325 mg of ASA every other day had a 44% reduction in the incidence of first myocardial infarction, and a 25% reduction in the incidence of subsequent myocardial infarction, stroke, and death from cardiovascular causes. Milani R V, Lavie C J, *Postgraduate Medicine* 1996;99(2):109–120.

NSAIDs fall into seven major classes: proprionic acid derivatives, indole derivatives, fenamates, pyrrolealkanoic acids, pyrazolone derivatives, oxicams and salicylic acids. NSAIDs for purposes of this invention are selected from, but not limited to acetylsalicylic acid, ibuprofen, naproxen and ketoprofen. Most develop some erosions in the stomach after each dose. The number of NSAID users presenting with serious GI complications is low (1–2%), but the high usage of NSAIDs means the number affected is large. The annual death rate amongst patients with rheumatoid and osteoarthritis due to serious adverse consequences of GI ulceration (perforation and hemorrhage) has been estimated at 16,500 in the US alone.

High gastric acidity contributes to NSAID injury to the stomach and duodenal bulb. Most NSAIDs are weak acids (pKa values 3.5 to 6) existing in a non-ionized form at low pH, and are lipid soluble. They readily diffuse into surface cells and become trapped at the higher intracellular pH. This accumulation causes local toxicity. Gastric acid and possibly pepsin, appears to deepen some of the superficial lesions that occur with NSAIDs. Most superficial lesions repair within 1–2 hours, but some patches of damaged tissues do not repair in time to prevent deeper tissue destruction.

The critical factor is how fast ASA is absorbed to reduce thrombosis within the 2 hour time frame. Enteric-coated ASA takes about 60 minutes to reach peak blood levels; regular ASA reaches peak blood levels in 30 minutes; but chewing an ASA tablet reaches blood levels and inhibits platelet activity in 5 minutes. Undissolved tablets and large particles that adhere to the gastric mucosa result in lesions. Micropulverized ASA particles, 100–600 µm, cause fewer lesions because they diffuse readily reducing contact with the gastric mucosa.

The dosage of ASA for the present invention consists of 325 mg per day which may be in divided dose when mixed with the amino sugar and zinc compound.

A number of patents disclose the use of ASA, primarily as analgesics both systemically and topically. Cotty et al, U.S. Pat. No. 4,049,803, discloses a composition of acetaminophen, ASA and caffeine. Patel, U.S. Pat. No. 4,867,984, discloses beads of ASA or acetaminophen coated with PVP. Frisbee, U.S. Pat. No. 4,970,081, discloses a formulation for a controlled release aspirin tablet. Bru et al, U.S. Pat. No. 5,437,874, discloses a composition of ASA or carbasalate calcium, metoclopramide, a hydrophilic polymer, anhydrous magnesium citrate and lactose. Eickhoff et al, U.S. Pat. No. 5,518,738, discloses NSAID particles coated with PVP. Liversidge et al, U.S. Pat. No. 5,552,160, discloses surface modified NSAID nanoparticles. Moshyedi, U.S. Pat. No. 5,770,215, discloses a vitamin supplement with ASA. Medford et al, U.S. Pat. No. 5,846,959, discloses a method for treating CVD with PUFA and CV drugs. Riley et al, U.S. Pat. No. 5,948,443, discloses a method for treating nutritional losses and heart disease with ASA, multivitamins and minerals. Noack et al, U.S. Pat. No. 5,973,011, discloses a method of treating endothelial dysfunction with PETN and active compounds to treat CVD. Weissman et al, U.S. Pat. No. 6,121,249, discloses a method for treating CVD with ASA, antioxidants and vitamins. Calanchi et al, U.S. Pat. No. 6,261,602 B1, discloses a microencapsulated mixture of thickening agents, disintegrating agents and pharmaceutically active substances.

NSAIDs inhibit prostaglandin (PG) synthesis by blocking the action of cyclooxygenase (COX), which exists in two forms. COX-1 is present in virtually all tissues and synthesizes PG, which provides GI mucosal protection. COX-2 is activated in response to cytokines and other inflammatory factors. NSAIDs currently available inhibit both COX-1 and COX-2 to varying degrees. Selective COX-2 inhibitors, Vioxx (rofecoxib) and Celebrex (celecoxib) were promoted to provide pain relief and avoid GI complications. However, all NSAIDs, including COX-2 inhibitors, can cause GI adverse events, including life-threatening perforations, ulcers or bleeds. One study comparing Vioxx to naproxen detected a four fold risk of myocardial infarction. Nissen S E, et al, *JAMA* 2001;286:954–959. COX-2 isoenzymes are necessary for maintaining renal blood flow. COX-2 inhibitors have also been reported to cause acute renal failure.

Platelets play an important role in the development of atherosclerosis. COX-2 inhibitors reduce the levels of prostacyclin (PGI2), a cyclooxygenase product that inhibits platelet activation and may accelerate atherosclerosis. Non-selective NSAIDs suppress both thromboxane and prostacyclin and retard atherogenesis. Pratico D, *Proc Natl Acad Sci USA* 2001;98:3358–3363. The cardioprotective effects of ASA are not seen with COX-2 inhibitors, which do not inhibit TXA2 production by platelets. Hart C, *Modern Drug Discovery* May/June 1999.

ASA has also been reported to be effective in reducing the risk of gastric cancer. Zaridze D, *Int J Cancer* 1999;82:473–476. ASA has also been reported to be effective against diabetic retinopathy, Alzheimers Disease, colon and rectal cancer, deep vein thrombosis, kidney failure, migraine headaches, cataracts, gallstones, and insect bites.

It is one object of this invention to incorporate an NSAID, such as ASA, to provide anti-inflammatory and anti-thrombotic benefits to prevent and treat endothelial dysfunction.

One of the gastrointestinal (GI) side-effects of nonsteroidal anti-inflammatory drugs (NSAIDs), is aggravating or initiating colitis type disorders, and explained by the hypothesis that NSAIDs inhibit glucosamine synthetase resulting in a reduction of the glucoaminoglycan (GAG) layer of the GI tract. The GAG layer is mechanical, located in the pre-endothelial and sub-endothelial area in the arterial network, and an electrostatic barrier, due to the negative charges from the highly anionic GAGs. The neutralization of the electrostatic barrier, results in a breakdown of the GAG defense, resulting in an increase in extravasation of body fluids into the intestinal lumen and also the passage of toxins and large foreign molecular weight antigens into the circulation. Russell A L, *Medical Hypothesis* 1999;52(4):297–301. There is a close histological and pathophysiological association with endothelial membrane changes in GI disorders and the endothelium of the vasculature. An atheroma occurs due to a defect in GAG function at the inflammation site of the endothelium allowing the defect to be saturated with cholesterol. Aminosugars such as glucosamine, chondroitin and synthetic mucopolysaccharide pentosam sulfate have been shown to replace the GAG layer and improve GI and vascular inflammatory disorders. Rheumatoid arthritis is believed due to increased permeability of the GI tract. Glucosamine, for purposes of this invention, may be regarded as a preventative of endothelium dysfunction.

Amino sugars, for purposes of this invention, consist of but are not limited to; glucosamine, glucosamine sulphate, glucosamine hydrochloride, N-acetylglucosamine and Poly-Nag. Glucosamine, which is formed in the body as glucosamine-6-phosphate (G6-P), is a building block for glycolipids, glycoproteins, glycosaminoglycans, hyaluronate and proteoglycans. It is an essential component of cell membranes and cell surface proteins as well as interstitial structural molecules that hold cells together.

Glucosamine is a small molecule, very soluble in water, and 90% absorbed in the GI tract. Glucosamine sulfate (GS) appears to be linked to its ability to stimulate the synthesis of proteoglycans needed to stabilize cell membranes and increase intracellular ground substance. Since the anti-inflammatory ability of GS is different than that of NSAIDs, it is possible the two might have a synergistic effect in alleviating some types of inflammation. Evidence indicates a combined treatment utilizing glucosamine with an NSAID can decrease the amount of NSAID required to produce an antiexudative result by a factor of 2–2.7 times with preservation of activity. Kelly G S, *Alt Med Rev* 1998;3(1):27–39.

The dosage range for glucosamine can vary from 200 mg to 3000 mg per day, in divided doses, for the treatment and prevention of endothelial dysfunction, osteoarthritis and inflammation, depending on body weight and severity of symptoms. The usual dosage is 500 to 1000 mg per day based on the amount of ASA used in each dosage. In a rapidly disintegrating tablet the amount of glucosamine is reduced due to the rapid absorption of the ASA in the oral cavity.

The use of amino sugars, such as glucosamine, is well known in the art. Jacobi, U.S. Pat. No. 3,859,436, discloses a topical composition of glucose, fructose, glucosamine and desoxyribose and ribose. Prudden, U.S. Pat. No. 4,006,224, discloses a method for treating ulcerative colitis with d-glucosamine. Henderson, U.S. Pat. No. 5,364,845, discloses a composition for the repair of connective tissue with glucosamine, chrondroitin sulfate and manganese. Sherman et al, U.S. Pat. No. 6,117,851, discloses a method for treating osteoarthritis.

It is a further object of this invention to incorporate an amino sugar, such as glucosamine, to enhance the GAG defense, anti-inflammatory properties, and synergistic effect with NSAIDs to treat and prevent endothelial dysfunction.

Zinc is known to have gastroprotective effects in both humans and experimental animals. Gastric lesions were induced in rats by the intragastric administration of indomethacin. Mucosal ulcerations were completely prevented by pre-treatment with zinc sulphate. These protective effects result from the inhibition of lipid peroxidation and the preservation of mucosal nitric oxide synthase. Joseph R M, Varela V, Kanji V K, Subramony C, Mihas A A, *Aliment Pharmacol Ther* 1999 February;13(2):203–8. Zinc sulphate taken orally was shown to heal gastric ulcers at three times the rate of a placebo. Zinc sulphate taken orally appears to act by the local action of zinc ions on the gastric mucosa. Frommer D J, *Med J of Australia* 1975;2:793–796.

Zinc compounds have anti-inflammatory and anti-infective properties. Zinc has an inhibitory effect on the release of histamine from mast cells due to its stabilizing effect of the mast cell membrane. Mast cells isolated from specimens of atherosclerotic plaques contained matrix metalloproteinase type 9, one of the enzymes that can produce collagen degradation. Kovanen Pt, et al. *J. Am College of Cardiology* 1998;32:606–612. Zinc can inhibit the growth of *Streptococci* and *Actinomyces* bacteria when used as a dentifrice. Zinc compounds have antiseptic, antifungal and astringent properties. As an astringent, zinc can be used therapeutically to arrest hemorrhage by coagulating blood, check diarrhea, reduce inflammation of mucus membranes, promote healing, toughen skin and decrease sweating. Zinc's dominant biological action is membrane stabilization. The inhibitory effect of zinc on allergy and immunology make it an excellent enhancement to glucosamine and chondroitin therapy.

One of the side effects of ASA is salicylate inducted hearing loss and tinnitus. The inner ear has the highest concentration of zinc in the body. Studies have suggested that a zinc deficiency can cause a hearing-nerve impairment and tinnitus. Shambaugh G E Jr., *Am J Otol* 1989 Mar; 10(2): 156–60. Salicylate-induced hearing loss was completely prevented by the simultaneous administration of zinc. Gunther T, Rebentisch E, Vormarn J, *J Trace Elem Electrolytes Health Dis* 1989 March;3(1):51–3. Zinc was also found to be useful in treating tinnitus. Ochi K, Ohashi T, et al *Nippon Jibiinkoka Gakkai Kaiho* 1997 September:100(9):915–9.

In a preferred form of the invention, the composition uses a zinc salt such as zinc gluconate or sulphate, with the dosage range of 10 to 60 mg per day in divided doses. Zinc salts are selected from a group consisting of, but not limited to: zinc sulfate, zinc chloride, zinc acetate, zinc phenol sulfonate, zinc borate, zinc bromide, zinc nitrate, zinc glycerophosphate, zinc benzoate, zinc carbonate, zinc camosine, zinc citrate, zinc hexafluorosilicate, zinc diacetate trihydrate, zinc oxide, zinc peroxide, zinc salicylate, zinc silicate, zinc stannate, zinc tannate, zinc titanate, zinc tetrafluoroborate, zinc gluconate, and zinc glycinate.

It is a further object of this invention to incorporate a zinc compound, such as zinc gluconate or sulphate, to reduce inflammation, prevent gastric ulceration, prevent toxic side effects of NSAIDs, and treat and prevent endothelial dysfunction. The amount of a zinc compound is reduced when a rapidly disintegrating tablet is used because the agents are absorbed in the oral cavity.

Hypertension contributes to endothelial dysfunction, particularly in coronary vessels. Mild hypertension is defined as a systolic pressure of 140 to 159 mm Hg and a diastolic pressure of 90 to 99 mm Hg. Untreated hypertension increases the incidence of stroke, coronary events, heart and renal failure and shortens life expectancy. Atherosclerosis is much more likely to appear in those parts of the circulatory system subjected to the highest blood pressure. In human hypertension, endothelial dysfunction has been documented in peripheral and coronary macro- and microcirculation and in renal circulation. Taddei S et al, *J Cardiovasc Pharmacol* 1998;32 Suppl (3):S41–7.

Dietary supplements that have been associated with lowering blood pressure or improving endothelial dysfunction and immune dysfunction include, but are not limieted to; calcium, magnesium, potassium, Coenzyme Q10, Vitamin A, Vitamin B, Vitamin C, Vitamin D, Vitamin E, L-arginine, flaxseed and fish oils, taurine, garlic, chromium, L-glutamine, glutathione, selenium, alpha-lipoic acid, folic acid, hawthorn, licorice extract, pantothenic acid, zinc, and various herbs and botanicals.

Reversing oxidative stress and the subsequent inhibition of lipid peroxidation should improve endothelial dysfunction. Vitamin E supplements, 600 mg per day, in a double-blind trial showed improvement in endothelial-dependent dilation of the brachial artery. Vitamin C improved vascular dysfunction in diabetics. The combined effects of Vitamin C and E prevented endothelial dysfunction during transient hyperglycemia after oral glucose loading in healthy subjects. Guerci B, et al, *Diabetes Metab* (*Paris*) 2001, 27: 436–447.

Vasoprotective supplements such as Vitamins C and E, calcium, omega-3 fatty acids, L-arginine, folic acid will improve endothelial function. Supplementation with folic acid and vitamin B12 improved brachial artery endothelium-dependent dilation in patients with CHD and that this action may be mediated through reduced concentrations of free plasma homocysteine. Chambers J C, et al, *Circulation* 2000;102:2479–2483.

Ascorbic acid (Vitamin C) reverses endothelial motor dysfunction in patients with coronary artery disease. Investigators found that long-term ascorbic acid treatment has a sustained beneficial effect on endothelium-derived nitric oxide action. Vita J A, *Circulation* 1999;99:3234–3240. Vitamin C was also found to reverse endothelial function in cardiomyopathy. Figulla H R, et al, *Am J Cardio* 2001;88:1001–1005. Doses of 500 mg/day lowered systolic blood pressure by 10% after one month.

Coenzyme Q10 (CoQ), a natural substance produced by the body, belongs to a family of compounds called quinines.

CoQ therapy in doses of 50 mg/twice a day can reduce blood pressure and stabilize blood glucose levels. Hodgson J M, *Eur J Clin Nutr* 2002;56:1137–1142. Similar results were obtained with calcium salts andalpha-lipoic acid supplementation. Vasdev S, et al, *J Hypertens* 2000 May;18(5):567–73.

Magnesium intake of 10 to 40 mmol is associated with reductions in blood pressure. Miller E R, et al, *Am J hypertens* 2002;15:691–696. Oral magnesium and potassium salts contribute to the electrical stability of the heart. Zehender M, et al, *J Am Coll Cardiol* 1997;29:1028–1034. Magnesium oral doses range from 10–50 mg but can be reduced with fast dissolving tablets. Potassium supplementation can prevent and treat hypertension, especially in those who are unable to reduce their sodium intake. Whelton P K, *Semin Nephrol* 1999 September;19(5):494–9. Modest increases in dietary potassium of 48 to 60 mmol/day lowers blood pressure in elderly hypertensive subjects. Fotherby M D, *Int J Clin Pract* 1997 June;51(4):219–22.

The enzyme nitric oxide synthase generates nitric oxide (NO) from the amino acid L-arginine. NO is responsible for vasodilator tone in the coronary arteries and the regulation of blood pressure in the systemic arteries. Arginine supplementation reverses endothelial dysfunction and lowers blood pressure. Siani A, et al, *Am J Hypertens* 2000 May;13(5 Pt 1):547–51. Oral dose of L-arginine ranges for 50–5,000 mg.

To the mixture may also be added; dyes, flavorings, sweeteners, pigments, antioxidants, antibacterial agents, anti-inflammatory agents, bismuth compounds, such as those known to persons skilled in the art may be added in amounts sufficient to impart their particular characteristic.

The above-mentioned patents are hereby incorporated by reference.

Many variations of the present invention will suggest themselves to those skilled in the art in light of the above-detailed description. All such obvious modifications are within the full intended scope of the appended claims.

REFERENCES

Alberts M, Baby aspirin, coated aspirin may not prevent stroke, American Stroke Assn, Phoenix, Ariz., Feb. 14, 2003.
Caligiuri G, Immune system activated in patients with unstable angine *J Am Coll Cardiol* 1998;32:1295–1304.
Chambers J C, et al, Improved Vascular Endothelial Function after Oral B Vitamins, *Circulation* 2000;102:2479–2483
Di Napoli M, C reactive proteins and acute pahse of ischemic stroke *BMJ* 2001;322:1605.
Feldman M, Cryer B, Chewing aspirin hastens its antiplatelet effect *Am J Cardiol* 1998;84:404–409.
Figulla H R, Vitamin C reverses impaired endothelial function in cardiomypoathy, *Am J Cardio* 2001;88:1001–1005.
Fotherby M D, Potter J F, Long-term potassium supplementation lowers blood pressure in elderly hypertensive subjects, *Int J Clin Pract* 1997, June;51(4):219–22.
Frommer D J, The Healing of Gastric Ulcers by Zinc Sulphate *Med J of Australia* 1975;2:793–796.
Guerci B, et al, Endothelial dysfunction and Type 2 Diabetes, *Diabetes Metab (Paris)* 2001, 27, 436–447.
Gunther T, Rebentisch E, Vormann J, Protection against salycialte ototoxicity by zinc *J Trace Elem Electrolytes Health Dis* 1989 March;3(1):51–3.
Hart C, Will Super Aspirin Supersede Aspirin *Modern Drug Discovery* May/June 1999.
Hingorani A D, et al., New explanation proposed for link between inflammation and cardiac events *Circulation* 2000;102:994–999.
Joseph R M, Varela V, Kanji V K, Subramony C, Mihas A A, Protective effects of zinc in indomethacin-induced gastric mucosal injury: evidence for a dual mechanism involving lipid peroxidation and nitric oxide *Aliment Pharmacol Ther* 1999 February;13(2):203–8.
Kelly G S, The Role of Glucosamine Sulphate and Chondroitin Sulfates in the Treatment of Degenerative Joint Disease *Alt Med Rev* 1998;3(1):27–39.
Knarbanda R K, et al, Prevention of inflammation—induced endothelial dysfunction: A novel vasculo-protective action of aspirin, *Ciorculation* 2002, June 4;105(22):2600–4.
Kuller L H, Tracy R P, The Role of Inflammation in Cardiovascular Disease *Arteriosclerosis, Thrombosis, and Vascular Biology* 2000;20(4):901
Malik J, Melenovsky V, Wichterle D, Function and dysfunction of the endothelium, *Cas Lek Cesk* 2000 "April 12;139(7):197–202.
Milani R V, Lavie C J, Pharmacologic prevention of coronary artery disease *Postgraduate Medicine* 1996;99(2):109–120.
Miller E R, Meta-analysis supports inverse link between magnesium intake and blood pressure, *Am J Hypertens* 2002;15:691–696.
Nissen S E, et al, COX-2 inhibitors linked to increased cardiovascular event rate *JAMA* 2001;286:954–959.
Ochi K, Ohashi T, Kinoshita H, Akagi M, Kikuchi H, Mitsui M, Kaneko T, Kato I, Serum zinc level in patients with tinnitus and the effect of zinc treatment *Nippon Jibiinkoka Gakkai Kaiho* 1997 September:100(9):915–9.
Pagano S A, et al, Blood Pressure and metabolic changes during dietary L-arginine supplementation in humans, *Am J Hypertens* 2000 May;13(5 pt 1):547–51.
Pepine, C J, Clinical implications of endothelial dysfunction, *Clin Cardiol* 1998 November;21(11):795–9.
Poredos P, Endothelial dysfunction in the pathogenesis of atherosclerosis, *Int Angiol* 2002 June;21(2):109–16.
Pratico D, Aspirin and other nonspecific COX inhibitors may slow atherosclerosis *Proc Natl Acad Sci USA* 2001;98:3358–3363.
Quyyumi A A, Endothelial Function in Health and Disease: New Insights into the Genesis of Cardiovascular Disease *Am J of Medicine* 1998;105(1A):32S–39S.
Rawles J, Importance of Thrombolytic Therapy *Pre-Hospital Immediate Care* 1997;1:12–18.
Ridker P M, Inflammation, Infection, and Cardiovascular Risk *Circulation* 1998;97:1671–1674.
Ridker P M, Cushman M, Stampfer M J, et al, Inflammation, Aspirin, and the Risk of Cardiovascular Disease in Apparently Healthy Men *NEJM* 1997;336(14):973–979.
Russell A L, Glycoaminoglycan (GAG) deficiency in protective barrier as an underlying, primary cause of ulcerative colitis, Crohn's disease, interstitial cystitis and possibly Reiter's syndrome *Medical Hypothesis* 1998;52(4):297–301.
Sandercock P A G, Aspirin administration recommended after Ischemic Stroke Onset *Lancet* 1997;349:1563–1565, 1569–1581.
Shambaugh G E Jr., Zinc: the neglected nutrient *Am J Otol* 1989 March;10(2):156–60.
Spencer F A, et al, Aspirin use reduces severity of acute coronary syndrome in CAD patients, *Am J Cardiol* 2002;90:1056–1061.
Taddei S, et al, Endothelial dysfunction in hypertension: fact of fancy?, *J Cardiovasc Pharmacol* 1998;32(Suppl 3):S41–7.
Tierney Jr. L M, McPhee S J, Papadakis M A, Current Medical Diagnosis and Treatment, Appelton & Lange, Norwalk, Conn., 3$^{rd}$ ed 1994 p.490.

Tindall W N, Cardiac Rehab: Movement and medication *Business & Health* February 1998.

Vallance P, Aspirin prevents inflammation-induced endothelial dysfunction, *Circulation* 2002 May 14;105(22).

Vasdev S, et al, Dietary alpha-lipoic acid supplementation lowers blood pressure in spontaneously hypertensive rats, *J Hypertens* 200 May;18(5):567–73.

Vita J A, Ascorbic acid improves vasodilation in patients with coronary artery disease, *Circulation* 1999;99:3234–3240.

Ward S R, Topol E J, New Strategies for the Prevention of Restenosis after Coronary Angioplasty *Resident & Staff Physician* 1995;41(3):11–18.

Whelton Pk, He J, Potassium in preventing and treating high blood pressure, *Semin Nephrol* 1999 September;19(5): 494–9.

Zaridze D, Aspirin, other NSAIDs help prevent gastric cancer *Int J Cancer* 1998;82:473–476.

Zehender M, et al, Antiarrhythmic effects of increasing the daily intake of magnesium and Potassium in patients with frequent ventricular arrythmias, *J Am Coll Cardiol.* 1997;29:1028–34.

| Patents: | | |
|---|---|---|
| 3,859,436 | Jan. 7, 1975 | Jacobi |
| 4,006,224 | Feb. 1, 1977 | Prudden |
| 4,049,803 | Sep. 20, 1977 | Cotty et al |
| 4,867,984 | Sep. 19, 1989 | Patel |
| 4,970,081 | Nov. 13, 1990 | Frisbee |
| 5,364,845 | Nov. 15, 1994 | Henderson |
| 5,437,874 | Aug. 1, 1995 | Bru et al |
| 5,518,738 | May 21, 1996 | Eickhoff et al |
| 5,552,160 | Sep. 3, 1996 | Liversidge et al |
| 5,770,215 | Jan. 23, 1998 | Moshyedi |
| 5,846,959 | Dec. 8, 1998 | Medford et al |
| 5,948,443 | Sep. 7, 1999 | Riley et al |
| 5,973,011 | Oct. 26, 1999 | Noack et al |
| 6,117,851 | Sep. 12, 2000 | Sherman et al |
| 6,121,249 | Sep. 19, 2000 | Weissman et al |
| 6,261,602B1 | Jul. 17, 2001 | Calanehi et al |

What is claimed is:

1. A composition for the treatment and prevention of endothelial dysfunction in mammals comprising a therapeutically effective amount of anti-inflammatory agents comprising; acetylsalicylic acid, an amino sugar and a zinc compound, combined with dietary supplements.

2. The composition according to claim 1, wherein the amino sugar is selected from a group comprising; glucosamine glucosamine hydrochloride, glucosamine sulfate, N-acetylglucosamine and mixtures thereof.

3. The composition according to claim 1, wherein the zinc compound is selected from a group comprising; zinc sulfate, zinc chloride, zinc acetate, zinc phenol sulfonate, zinc borate, zinc bromide, zinc nitrate, zinc glycerophosphate, zinc benzoate, zinc carbonate, zinc citrate, zinc hexafluorosilicate, zinc diacetate trihydrate, zinc oxide, zinc peroxide, zinc salicylate, zinc silicate, zinc stannate, zinc titanate, zinc tetrafluoroborate, zinc gluconate, and zinc glycinate.

4. The composition according to claim 1, wherein the dietary supplements are selected from a group comprising: calcium, potassium, magnesium, coenzyme Q10, arginine, alpha-lipoic acid, Vitamin A, Vitamin B, Vitamin C, Vitamin D, Vitamin E, folic acid, selenium, alpha-lipoic acid, herbs, botanicals and mixtures thereof.

5. The composition of claim 1, that is in the form of a powder to accelerate local and systemic absorption.

6. The composition of claim 1, that is optionally delivered in the form of a rapidly disintegrating tablet.

7. A composition for the treatment and prevention of endothelial dysfunction in mammals comprising a therapeutically effective amount of blood pressure lowering agents, an amino sugar, and a zinc compound in the form of a rapidly disintegrating tablet.

8. The composition according to claim 7, wherein the blood pressure lowering agents are selected from a group comprising; calcium, potassium, magnesium, coenzyme Q10, arginine, alpha-lipoic acid, Vitamin A, Vitamin B, Vitamin C, Vitamin D, Vitamin E, folic acid, selenium, flaxseed and fish oils, taurine, garlic, chromium, L-glutamine, glutathione, pantothenic acid, hawthorn, licorice extract, herbs, botanicals and mixtures thereof.

9. The composition according to claim 7, wherein the amino sugar is selected from a group comprising; glucosamine, glucosamine hydrochloride, glucosamine sulfate, N-acetylglucosamine and mixtures thereof.

10. The composition azinc compound of claim 7, wherein the zinc compound is selected from a group comprising; zinc sulfate, zinc chloride, zinc acetate, zinc phenol sulfonate, zinc borate, zinc bromide, zinc nitrate, zinc glycerophosphate, zinc benzoate, zinc carbonate, zinc citrate, zinc hexafluorosilicate, zinc diacetate trihydrate, zinc oxide, zinc peroxide, zinc salicylate, zinc silicate, zinc stannate, zinc tannate, zinc titanate, zinc tetrafluoroborate, zinc gluconate, and zinc glycinate.

11. A method for the treatment and prevention of endothelial dysfunction in mammals by administering to the mammals a therapeutically effective amount of anti-inflammatory agents comprising; acetylsalicylic acid, an amino sugar and a zinc compound combined with dietary supplements.

12. The method of claim 11, wherein the amino sugar is selected from a group comprising; glucosamine, glucosamine hydrochloride, glucosamine sulfate, N-acetylglucosamine and mixtures thereof.

13. The method of claim 11, wherein the zinc compound is selected from a group comprising; zinc sulfate, zinc chloride, zinc acetate, zinc phenol sulfonate, zinc borate, zinc bromide, zinc nitrate, zinc glycerophosphate, zinc benzoate, zinc carbonate, zinc citrate, zinc hexafluorosilicate, zinc diacetate trihydrate, zinc oxide, zinc peroxide, zinc salicylate, zinc silicate, zinc stannate, zinc tannate, zinc titanate, zinc tetrafluoroborate, zinc gluconate, and zinc glycinate.

14. The method of claim 11, wherein the dietary supplements are selected from a group comprising; calcium, potassium, magnesium, coenzyme Q10, arginine, alpha-lipoic acid, Vitamin A, Vitamin B, Vitamin C, Vitamin D, Vitamin E, folic acid, selenium, flaxseed and fish oils, taurine, garlic, chromium, L-glutamine, glutathione, pantothenic acid, hawthorn, licorice extract, herbs, botanicals and mixtures thereof.

15. The method of claim 11, wherein the composition is in the form of a powder to accelerate local and systemic absorption.

16. The method of claim 11, wherein the composition is optionally in the form of a rapidly disintegrating tablet.

17. A method for the treatment and prevention of endothelial dysfunction in mammals comprising administering to the mammals a therapeutically effective amount of blood pressure lowering agents, an amino sugar, and a zinc compound.

18. The method of claim 11 or 17, wherein the composition may contain one or more agents selected from a group comprising; flavorings, sweeteners, pigments, antioxidants, immune stimulants, antibacterial agents, bismuth compounds, and anti-inflammatory agents.

* * * * *